United States Patent
Karlinsey

(10) Patent No.: US 8,603,441 B2
(45) Date of Patent: *Dec. 10, 2013

(54) FUNCTIONALIZED CALCIUM PHOSPHATE HYBRID SYSTEMS FOR CONFECTIONERY AND FOODSTUFF APPLICATIONS

(75) Inventor: Robert L. Karlinsey, Indianapolis, IN (US)

(73) Assignee: Indiana Nanotech LLC, Indianapolis, IN (US)

(*) Notice: Subject to any disclaimer, the term of this patent is extended or adjusted under 35 U.S.C. 154(b) by 1329 days.

This patent is subject to a terminal disclaimer.

(21) Appl. No.: 12/210,137

(22) Filed: Sep. 12, 2008

(65) Prior Publication Data

US 2010/0068159 A1  Mar. 18, 2010

(51) Int. Cl.
| A61Q 11/00 | (2006.01) |
| A61Q 11/02 | (2006.01) |
| A61K 9/16 | (2006.01) |
| C01F 11/00 | (2006.01) |
| C08K 3/32 | (2006.01) |

(52) U.S. Cl.
CPC . *A61Q 11/00* (2013.01); *A61K 9/16* (2013.01); *A61K 9/1611* (2013.01); *A61K 9/1617* (2013.01); *A61Q 11/02* (2013.01); *C01F 11/00* (2013.01); *C08K 2003/325* (2013.01)
USPC .................. 424/49; 409/64; 424/57; 424/489

(58) Field of Classification Search
USPC .......................................... 424/52
See application file for complete search history.

(56) References Cited

U.S. PATENT DOCUMENTS

| 3,190,568 | A | 6/1965 | Freedman et al. |
| 3,876,160 | A | 4/1975 | Bloch |
| 4,018,619 | A | 4/1977 | Webster et al. |
| 4,677,140 | A | 6/1987 | Shioitsu |
| 5,342,441 | A | 8/1994 | Mandai et al. |
| 5,833,954 | A | 11/1998 | Chow et al. |
| 6,053,970 | A | 4/2000 | Ison et al. |
| 6,126,097 | A | 10/2000 | Chen et al. |
| 6,334,583 | B1 | 1/2002 | Li |
| 6,840,961 | B2 | 1/2005 | Tofighi et al. |
| 2002/0037258 | A1 | 3/2002 | Dodd et al. |
| 2003/0069638 | A1 | 4/2003 | Barlow et al. |
| 2003/0120351 | A1 | 6/2003 | Tofighi et al. |
| 2004/0101494 | A1* | 5/2004 | Scott et al. ........................ 424/49 |
| 2005/0025721 | A1* | 2/2005 | Holme et al. ..................... 424/48 |
| 2005/0241535 | A1 | 11/2005 | Bohner |
| 2006/0175443 | A1 | 8/2006 | Bysouth |
| 2006/0270752 | A1 | 11/2006 | Xu et al. |
| 2007/0059379 | A1 | 3/2007 | Gerber |
| 2007/0149650 | A1 | 6/2007 | Masuda |
| 2007/0178220 | A1 | 8/2007 | Karlinsey |
| 2007/0183984 | A1* | 8/2007 | Haas et al. ........................ 424/48 |
| 2008/0187500 | A1* | 8/2008 | Karlinsey ......................... 424/52 |

FOREIGN PATENT DOCUMENTS

| CA | 1089428 | 11/1980 |
| GB | 593777 | 10/1947 |
| WO | 0237258 | 3/2002 |

OTHER PUBLICATIONS

Park et al., Research about Tooth Whitening and Bacteria Sticking Capability with Using Dentifrice Including Nano-Hydroxyapatite, Sodium Metaphosphate, Key Engineering Materials, 2007, vol. (330-332), pp. 283-286.*

* cited by examiner

*Primary Examiner* — Frederick Krass
*Assistant Examiner* — Isaac Shomer
(74) *Attorney, Agent, or Firm* — Brannon Sowers & Cracraft PC

(57) ABSTRACT

A method of whitening teeth, including an application of functionalized calcium phosphate additives generated via a solid-state method. The additives were produced by placing predetermined amounts of inorganic and inorganic materials and milling media into a vessel rotatably connected to a turntable platform, an amount of an organic material into the vessel, rotating the vessel in a first direction while turning the turntable platform in a second direction counter to the first direction, with the resultant material defining the functionalized calcium phosphate. The inorganic material may include calcium phosphates of varying phases, structure, and composition. The organic material may include anionic surfactants, cationic surfactants, neutral surfactants, carboxylic acids, polymers, copolymers, block copolymers, and combinations thereof. Once produced, the additives were added to comestibles, such as in confectionery and foodstuff formats, for delivery to the teeth and dental structures.

6 Claims, No Drawings

FUNCTIONALIZED CALCIUM PHOSPHATE HYBRID SYSTEMS FOR CONFECTIONERY AND FOODSTUFF APPLICATIONS

CROSS-REFERENCE TO RELATED APPLICATIONS

This application claims priority to co-pending utility patent application Ser. No. 12/018,627 filed Jan. 23, 2008; U.S. provisional patent application Ser. No. 60/888,354, filed Feb. 6, 2007; U.S. provisional patent application Ser. No. 60/891,849, filed Feb. 27, 2007; and U.S. provisional patent application Ser. No. 60/941,095, filed May 31, 2007, each of which are incorporated herein in their entirety by reference.

TECHNICAL FIELD

The present novel technology relates generally to the application of functionalized hybrid moieties to mints, gums, lozenges, and other confectionery or foodstuff formats to provide improved therapeutic and cosmetic dental benefits.

BACKGROUND

Preventing caries and cavities and improving the delivery of minerals necessary to healthy teeth, while preserving and/or enhancing cosmetic features, are important goals in oral health care. While preventive products can be extremely effective, sometimes the action of these products cannot keep up with consumer/patient habits (e g. diet, hygiene, salivary flow, saliva constituents, etc). In this regard, the chewing or dissolution of sugar free products, such as gums, lozenges, and mints, after or in between eating events may be recommended since studies show the ensuing saliva stimulation can effectively remineralize teeth. Although the stimulated saliva is effective, there are opportunities to further improve efficacy by delivering calcium and phosphate to the dentition. Unfortunately, conventional calcium phosphate materials technologies are only marginally effective in providing useful minerals to teeth.

Clearly then, there is a need for mineral delivery compounds that can help boost remineralization efficacy, while whitening enamel, through confectionery and foodstuff formats, such as a mint, gum, or lozenge. The present novel technology discussed herein addresses this need.

Thus, there remains a need for a process for more efficiently producing functionalized materials that may compliment new and/or existing confectionery and foodstuff formulations, such as mints, gums, lozenges, and the like, to provide therapeutic and cosmetic dental benefits. The present novel technology addresses these needs.

SUMMARY

The present novel technology relates generally to the inclusion of functionalized hybrid moieties to mints, gums, lozenges, and other confectionery and foodstuff formats in order boost remineralization efficacy of the dentition, as well as provide cosmetically-important whitening of the enamel.

One object of the present novel technology is to provide an improved method for producing functionalized hybrid moieties for the purposes of delivering superior performance in mints, gums, and other confectioneries and foodstuffs. Further objects, features, and advantages will become apparent from a consideration of the following description.

DETAILED DESCRIPTION

For the purposes of promoting an understanding of the principles of the novel technology, reference will now be made to the embodiments illustrated in the drawings and specific language will be used to describe the same. It will nevertheless be understood that no limitation of the scope of the novel technology is thereby intended, such alterations and further modifications in the illustrated device, and such further applications of the principles of the novel technology as illustrated therein being contemplated as would normally occur to one skilled in the art to which the novel technology relates.

The present novel technology includes a method for producing a thermodynamically and kinetically stable material that slowly releases ions and moieties due to the complex chemistry created during the alloying process. The technique was developed in part to address a need for, among other things, improved mints, gums, lozenges, and other confectionery and foodstuff formats. Accordingly, the following examples and embodiments tend to reflect chemistries having dental applications. However, the present application is broadly applicable beyond the dental applications discussed herein.

One aspect of the present novel technology relates to the application of functionalized hybrid materials to provide improved dental benefits by delivering small, surfactant-coated minerals to a substrate, such as dentition. The functionalized surface aids in promoting direct contact between a target material (such as the pellicle, enamel, or the like), and therefore allows for more efficient delivery of a desired mineral component (such as calcium and phosphate).

The novel chemical synthesis method exploits the mechanochemical ball milling process to produce a relatively great amount of relatively inexpensive functionalized complexes. Typically, the functionalized complexes are blends of independent organic and inorganic reagents coupled together to yield a hybrid material with enhanced properties. A typical inorganic reagent generally includes a calcium phosphate mineral such as calcium phosphate tribasic, calcium phosphate dibasic, dicalcium phosphate, and the like. Alternatively, other inorganic materials may include sodium, magnesium, iron, silicon, aluminum, manganese, titanium and the like in various mineralogical forms (such as carbonates, nitrides and the like).

Typical organic reagents include anionic surfactants, cationic surfactants, neutral surfactants—polyethers or polyesters, carboxylic acids, polymethyl methacrylate, or the like. In other words, the organic reagents may include those materials with properties akin to those species listed above.

For example, hybrid calcium phosphate-fumaric acid systems may be produced in various formulations for improving remineralization efficacy of a mint, gum, lozenge, or the like. The hybrid synthesis process is described below.

Hybrid Synthesis

The preparation of organic-inorganic materials via a mechanochemical process is described as follows. Depending upon the desired composition, the mixture may range from between about 0.5 and 99.5 weight percent inorganic precursor material, with the balance being organic precursor material. In this example, the inorganic starting material is tricalcium phosphate, while the organic starting material is fumaric acid; however, any convenient inorganic and organic precursors may be selected. Tricalcium phosphate (TCP, $Ca_3(PO_4)_2$) plus fumaric acid (FA) may be combined to define an admixture. The admixture is typically added to a vessel containing a plurality of milling media balls, such as ten 20 millimeter diameter balls. The admixture typically contains between about 0.1 and 20 weight percent FA with the balance substantially TCP. Additionally, a small amount of an organic solvent, such as pentane, may be added as a lubricant. Once loaded with the admixture and milling media, the vessel is typically locked onto the sun wheel of a planetary ball mill. The vessel is then rotated unidirectionally and opposite the rotational direction of the sun wheel at a sufficiently high speed for a duration of time sufficient to yield functionalized chemical moieties, such as, for example, at least about 400 rpm for about two hours. At the end of the milling process the resulting powder is substantially composed of functionalized moieties. The powder is then filtered from the balls and stored, such as in plastic containers. The powder may also be sized, such as through a sieving process, prior to storage.

After the functionalized moieties are recovered in powder form, they are added to comestibles to yield an improved dental repair product. Such comestibles may include candies, mints, gums, lozenges and the like.

EXAMPLE 1

Pre-In Situ Cross-Over Study Exploring a TCP-FA Additive in Remineralization Model Purpose One purpose of this study was to evaluate in a pH remin/demin cycling model the potential efficacy of a functionalized calcium phosphate powder (TCP90FA10 = 90 wt. % TCP plus 10 wt. % FA) in remineralizing white-spot enamel lesions via a sugarless chewing gum format. To better emulate 'real' chewing gum scenarios, sticks of a sugar free chewing gum were chewed by human subjects, with the resulting saliva generated during the event used as the 'treatment'.

Specimen Preparation

Bovine enamel specimens (3 mm) were ground and polished using standard methods.

Three groups (N=10) of specimens were prepared for this study.

Artificial lesions were formed in the enamel specimens by immersion into a carbopol-lactic acid solution which had been saturated with hydroxyapatite and adjusted to pH 5.0 at 37° C.

Study Design

Three treatment groups were in the study:

Group 1: DI Water

Group 2: Sugar free gum

Group 3: Sugar free gum+0.5% TCP90FA10

Subjects chewed gum and expectorated saliva into cups which were then used as the treatments;

Four 20-minute treatment periods and three 20-minute acid challenge periods were given daily with the remainder of the time the specimens were immersed in artificial saliva;

Enamel specimens (N=10 for each group) 'cycled' for 5 days in artificial saliva (pH=7), in a carbopol-lactic acid challenge (pH=5), and in expectorated saliva (pH between 7 and 8);

After 5 days specimens were analyzed for surface microhardness as shown in Table 1;

New enamel specimens were then used and cycled for another 5 days with subjects alternating treatments—results shown in Table 2;

TABLE 1

Remineralization determined via Vickers surface microhardness after 5 days of pH cycling.

| Group | Mean $\Delta VHN \pm SEM$ |
|---|---|
| [1]DI Water | $6.4 \pm 0.6$ |
| [2]Sugarfree gum | $9.5 \pm 1.3$ |
| [3]Sugarfree gum + 0.5% TCP90FA10 | $16.0 \pm 1.0$ |

Superscripts indicate significant differences ($p < 0.05$, one-way ANOVA, SNK method), where $1 < 2 < 3$.

TABLE 2

Remineralization determined via Vickers surface microhardness after 5 days of pH cycling.

| Group | Mean $\Delta VHN \pm SEM$ |
|---|---|
| [1]DI Water | $3.4 \pm 0.9$ |
| [2]Sugarfree gum | $6.5 \pm 0.5$ |
| [3]Sugarfree gum + 0.5% TCP90FA10 | $10.2 \pm 0.9$ |

Superscripts indicate significant differences ($p < 0.05$, one-way ANOVA, SNK method), where $1 < 2 < 3$.

Results:

Cross-over study demonstrated model validity;

Efficacy of TCP90FA10 was demonstrated

TCP-FA provided an additional 62% remineralization improvement

EXAMPLE 2

Pre-In Situ Study Evaluating the TCP-FA Additive Versus a Competitive Calcium Phosphate Technology in a Remineralization Model Purpose The purpose of this pilot study was to evaluate in a pH remin/demin cycling model the efficacies of TCP90FA10 versus a commercially available calcium phosphate material, RECALDENTO® (RECALDENT is a registered trademark of Cadbury Enterprises PTE LTD Limited Company, Singapore, 346 Jalan Boon Lay Jurong Singapore 61952) in remineralizing white-spot enamel lesions. This head-to-head comparison was used to investigate whether the TCP90FA10 calcium phosphate system can outperform RECALDENT® in a prospective chewing gum formulation. To better emulate 'real' chewing gum scenarios, sticks of a sugarless chewing gum and TRIDENT XTRA CARE® with RECALDENT® chewing gums were chewed by human subjects, with the saliva generated during the event used as the 'treatment' (TRIDENT XTRA CARE is a registered trademark of Cadbury Adams LLC, 389 Interpace Parkway, Parsippany, N.J. 07054).

Specimen Preparation

Bovine enamel specimens (3 mm) were ground and polished using standard methods.

Three groups (N=10) of specimens were prepared for this study.

Artificial lesions were formed in the enamel specimens by immersion into a carbopol-lactic acid solution which had been saturated with hydroxyapatite and adjusted to pH 5.0 at 37° C.

Study Design

Three treatments groups were in the study:

Group 1: DI Water

Group 2: Sugar free gum+0.1% TCP-FA system

Group 3: Trident XtraCare

Subjects chewed gum and expectorated saliva into cups which were then used as the treatments;

Four 20-minute treatment periods and three 20-minute acid challenge periods were given daily; during the remainder of the time the specimens were immersed in artificial saliva;

Enamel specimens (N=10 for each group) 'cycled' for 4 days in artificial saliva (pH=7), in a carbopol-lactic acid challenge (pH=5), and in expectorated saliva (pH between 7 and 8);

After 4 days specimens were analyzed for surface microhardness as shown in Table 3;

TABLE 3

Remineralization determined via Vickers surface microhardness after 5 days of pH cycling.

| Group | Mean ΔVHN ± SEM |
|---|---|
| [1]DI Water | 1.7 ± 0.4 |
| [3]Sugarfree gum + 0.1% TCP-FA | 10.0 ± 0.8 |
| [2]Trident Xtra Care | 3.8 ± 0.7 |

Superscripts indicate significant differences (p < 0.05, one-way ANOVA, SNK method), where 1 < 2 < 3.

Results:
  Split between DI water and gum systems demonstrated model validity;
  Efficacy of sugar free gum+0.1% TCP-FA provided an additional 162% remineralization improvement relative to Trident Xtra Care sugar free gum comprising the Recaldent® technology

EXAMPLE 3

Pre-In Situ Study Exploring the Potential of the TCP-FA Additive in Remineralizing and Whitening White-Spot Enamel Lesions Purpose The purpose of this study was to evaluate in a pH remin/demin cycling model the potential efficacy of a functionalized calcium phosphate powder (TCP90FA10 =90 wt. % TCP plus 10 wt. % FA) in remineralizing white-spot enamel lesions and whiten enamel via a sugarless chewing gum format. To better emulate 'real' chewing gum scenarios, sticks of a sugar free chewing gum were chewed by human subjects, with the resulting saliva generated during the event used as the 'treatment'.

Specimen Preparation

Bovine enamel specimens (3 mm) were ground and polished using standard methods.

Three groups (N=10) of specimens were prepared for this study.

Artificial lesions were formed in the enamel specimens by immersion into a carbopol-lactic acid solution which had been saturated with hydroxyapatite and adjusted to pH 5.0 at 37° C.

Study Design

Treatment groups:
  Group 1: Distilled water (negative control) treatment;
  Group 2: Sugar free chewing gum (positive control);
  Group 3: Sugar free chewing gum+0.1% TCP90FA10;

Subjects chewed gum and expectorated saliva into cups which were then used as the treatments;

Four 20-minute treatment periods and three 20-minute acid challenge periods were given daily with the remainder of the time the specimens were immersed in artificial saliva;

Enamel specimens (N=10 for each group) 'cycled' for 5 days in artificial saliva (pH=7), in a carbopol-lactic acid challenge (pH=5), and in expectorated saliva (pH between 7 and 8);

After 5 days specimens were analyzed for surface microhardness as shown in Table 4;

Using a calorimeter, specimens were then analyzed for color based on the Commission Internationale de l'Eclairage (CIE) Lab color space b* axis, which represents the yellowness (positive values, undesirable) or blueness (negative values, desirable), as shown in Table 4.

TABLE 4

Remineralization determined via Vickers surface microhardness after 5 days of pH cycling.

| Group | Mean ΔVHN ± SEM | b* |
|---|---|---|
| DI Water | 3.1 ± 0.9[1] | −15.1 ± 0.5[1] |
| Sugar free gum | 6.8 ± 1.4[2] | −15.5 ± 0.9[1] |
| Sugar free gum + 0.1% TCP90FA10 | 9.8 ± 1.3[3] | −16.7 ± 1.4[2] |

Superscripts indicate significant differences (p < 0.05, one-way ANOVA, SNK method), where 1 < 2 < 3.

Conclusion:
  Split between DI water and gum systems demonstrated model validity;
  Efficacy of sugar free gum+0.1% TCP-FA provided a statistically significant boost (44.1%) in remineralization relative to the control sugar free gum in this short-term study;
  The color of the specimens treated with the sugar free gum+0.1% TCP-FA was found to be statistically bluer (i.e. less yellow, more white) relative to the control sugar free gum (~8% whiter) in this short-term study;

Typically, functionalized moieties (such as TCP-FA compounds), are added to comestibles in concentrations of about 0.01 wt. % to about 1.0 wt. %, and more typically in concentrations of between about 0.05 wt. % and about 0.5 wt. %. The functionalized moieties may be added primarily as a surface treatment or distributed substantially uniformly through the comestible.

While the novel technology has been illustrated and described in detail in the foregoing examples, the same is to be considered as illustrative and not restrictive in character, it being understood that only the preferred embodiments have been shown and described and that all changes and modifications that come within the spirit of the novel technology are desired to be protected.

What is claimed is:

1. A method of treating teeth, comprising:
   a) combining a predetermined amount of tricalcium phosphate with a predetermined amount of an organic material to produce a mixture;
   b) placing the mixture into a milling vessel operationally connected to a planetary mill;
   c) introducing milling media into the milling vessel;
   d) milling said mixture to impart sufficient kinetic energy to break down the organic material and tricalcium phosphate into substantially smaller intermediate particles and fuse the intermediate particles together to yield a hybrid material having both organic and tricalcium phosphate characteristics;
   e) combining said hybrid material with a comestible to produce a hybrid system;
   f) applying the hybrid system to whiten teeth.

2. The method of claim 1 wherein said hybrid material comprises between 0.5 and 99.5 weight percent of tricalcium phosphate and between 0.5 and 99.5 weight percent of organic material.

3. The method of claim 1 wherein the organic material is a carboxylic acid selected from the group consisting of fumaric acid, acrylic acid, malic acid, citric acid, maleic acid, stearic acid and combinations thereof.

4. A method of whitening teeth, comprising:
   a) combining tricalcium phosphate with an organic acid to produce a mixture;
   b) imparting sufficient kinetic energy to said mixture by milling to break down said tricalcium phosphate and said organic acid into substantially smaller intermediate particles;
   c) fusing said intermediate particles together to produce a hybrid material with both organic and inorganic chemical characteristics;
   d) combining said hybrid material with a member selected from the group consisting of mints, gums, lozenges, confectioneries, and combinations thereof to produce a hybrid system; and
   e) applying said hybrid system to teeth.

5. The method of claim 4 wherein the organic acid is selected from the group consisting of fumaric acid, acrylic acid, malic acid, citric acid, maleic acid, stearic acid and combinations thereof.

6. A method of cosmetically remineralizing dentition comprising:
   a) combining tricalcium phosphate with an organic acid selected from the group consisting of fumaric acid, acrylic acid, malic acid, citric acid, maleic acid, stearic acid and combinations thereof to produce a mixture;
   b) imparting sufficient kinetic energy to said mixture by milling to break down said tricalcium phosphate and said organic acid into substantially smaller intermediate particles;
   c) fusing said intermediate particles together to produce a hybrid material with both organic and inorganic chemical characteristics;
   d) combining said hybrid material with a member selected from the group consisting of mints, gums, lozenges, confectioneries, and combinations thereof to produce a hybrid system; and
   e) applying said hybrid system to teeth.

* * * * *